(12) United States Patent
Banerjee et al.

(10) Patent No.: US 11,051,741 B2
(45) Date of Patent: Jul. 6, 2021

(54) NON-INVASIVE DETECTION OF CORONARY HEART DISEASE FROM SHORT SINGLE-LEAD ECG

(71) Applicant: Tata Consultancy Services Limited, Mumbai (IN)

(72) Inventors: Rohan Banerjee, Kolkata (IN); Sakyajit Bhattacharya, Kolkata (IN); Soma Bandyopadhyay, Kolkata (IN); Aniruddha Sinha, Kolkata (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 95 days.

(21) Appl. No.: 16/557,904

(22) Filed: Aug. 30, 2019

(65) Prior Publication Data
US 2020/0069205 A1 Mar. 5, 2020

(30) Foreign Application Priority Data
Aug. 30, 2018 (IN) .............................. 201821032504

(51) Int. Cl.
*A61B 5/025* (2006.01)
*A61B 5/316* (2021.01)
(Continued)

(52) U.S. Cl.
CPC .......... *A61B 5/316* (2021.01); *A61B 5/02405* (2013.01); *A61B 5/25* (2021.01);
(Continued)

(58) Field of Classification Search
CPC ....... A61B 5/316; A61B 5/25; A61B 5/02405; A61B 5/02108
See application file for complete search history.

(56) References Cited

FOREIGN PATENT DOCUMENTS

FR    3053238    1/2018

OTHER PUBLICATIONS

Liu, C. et al. (2011). "Evaluation method for heart failure using RR sequence normalized histogram," *Computing in Cardiology*, vol. 38; pp. 305-308.

(Continued)

*Primary Examiner* — Allen Porter
*Assistant Examiner* — Skylar Lindsey Christianson
(74) *Attorney, Agent, or Firm* — Finnegan, Henderson, Farabow, Garrett & Dunner LLP

(57) ABSTRACT

Electrocardiography (ECG) signals contain important markers for Coronary Heart Disease (CHD). State of the art systems and methods rely on clinically available multi-lead ECG for CHD classification which is not cost effective. Moreover the state of the art methods are applied on digital ECG time series data only. Also, discriminative HRV markers are not often present in short ECG recordings necessitating long hours of ECG data to analyze. In accordance with the present disclosure, systems and methods described hereinafter extract ECG time series from ECG images obtained from commercially available low-cost single lead ECG devices through a combination of image and signal processing steps including Histogram analysis, Morphological operation-thinning, Extraction of lines, Extraction of Reference Pulse, Extraction of ECG and interpolating missing data. Further, domain independent statistical features such as self-similarity of raw ECG time series and average Maharaj's distance along with domain specific features are used for classifying CHD.

8 Claims, 7 Drawing Sheets extracting a second set of features comprising domain specific statistical features pertaining to Heart Rate Variability (HRV), from RR interval time series ($RR_t$) obtained from the raw ECG time series, wherein the second set of features comprise one or more of range, standard deviation, kurtosis, skewness, ratio of spectral power content of the $RR_t$ between an empirically determined range of frequencies, Shannon entropy of the $RR_t$, pNNT indicative of a time domain measure of HRV based on the number of successive RR intervals ($m$) exceeding time $T$ in an ECG recording of a fixed duration, wherein time $T$ is measured in ms and $\delta RR_t$ time series is indicative of successive RR intervals ($RR_t - RR_{t-1}$), Normalized Root Mean Square of Successive Differences (*nRMSSD*), features from Lorenz plot of the $\delta RR_t$ time series including *AnisotropyEvidence* and *PACEvidence*, and features from recurrence plots of the $RR_t$ including recurrence rate (*REC*), determinism (*DET*) and mean diagonal line length ($L_{mean}$) /— 204 classifying the raw ECG time series into a CHD or a non-CHD candidate based on a complete feature set comprising the first set of features and the second set of features /— 206

(51) Int. Cl.
*A61B 5/024* (2006.01)
*A61B 5/25* (2021.01)
*A61B 5/00* (2006.01)
*A61B 5/021* (2006.01)

(52) U.S. Cl.
CPC ......... *A61B 5/02108* (2013.01); *A61B 5/7239* (2013.01); *A61B 5/7264* (2013.01)

(56) References Cited

OTHER PUBLICATIONS

Corduas, M. et al. (2008). "Time series clustering and classification by the autoregressive metric," *Computational Statistics & Data Analysis*, vol. 52; pp. 1860-1872.
Dua, S. et al. (2012). "Novel classification of coronary artery disease using heart rate variability analysis," *Journal of Mechanics in Medicine & Biology*, vol. 12; pp. 1240017-1 to 1240017-19.

200 —

202 — extracting a first set of features comprising domain independent statistical features, from an obtained raw electrocardiography (ECG) time series, wherein the first set of features include (i) self-similarity of the raw ECG time series indicative of a rate of decrease in autocorrelation with an increase in lag between a pair of observations, wherein the self-similarity is measured based on Hurst parameter ($H$) which is computed by fitting the raw ECG time series into a Fractional Autoregressive Integrated Moving Average (FARIMA($0,d,0$)) model by an approximation of the maximum likelihood method and the Hurst parameter is estimated using the relation $H=d+0.5$, wherein $d$ is a degree of differentiating indicative of the number of times the raw ECG time series has a past value subtracted from a current value and (ii) average Maharaj's distance indicative of a moving average factor along with the number of changes in direction of the raw ECG time series, wherein the average Maharaj's distance is based on the Maharaj's distance of the raw ECG time series of an $i^{th}$ subject from a $j^{th}$ coronary heart disease (CHD) subject in a training dataset and $nu$ being the total number of CHD subjects in the training dataset and measures the average dissimilarity of an ECG time series from the CHD population in the training dataset

NON-INVASIVE DETECTION OF CORONARY HEART DISEASE FROM SHORT SINGLE-LEAD ECG

PRIORITY CLAIM

This U.S. patent application claims priority under 35 U.S.C. § 119 to Indian Patent Application No. 201821032504, filed on Aug. 30, 2018. The entire contents of the aforementioned application are incorporated herein by reference.

TECHNICAL FIELD

The disclosure herein generally relates to identifying a risk of coronary heart disease (CHD), and, more particularly, to systems and methods for non-invasive detection of coronary heart disease from short single-lead electrocardiography (ECG).

BACKGROUND

Coronary heart disease (CHD) or Coronary artery disease (CAD) is a major cause of death in both developed and developing nations. Fatal consequences of heart diseases can often be avoided if detected at early stages. This indicates the importance of affordable, efficient and accurate disease screening systems. Numerous research works show that discriminative patterns can be found in biomedical signals like phonocardiogram (heart sound) or electrocardiogram (ECG) even at the onset of CAD. Heart Rate Variability (HRV) is a commonly used marker for CAD. Standard 12-lead clinical ECG devices, commonly used in prior art approaches for extraction of HRV parameters have severe deployment issues in realizing a low-cost screening system. Moreover, discriminative HRV markers related to CAD are not often present in short ECG recordings. This requires hours of ECG data to analyze. Automatic segregation of P, QRS and QT wave intervals from ECG for extraction of domain specific morphological features is also a challenging task with limited accuracy.

SUMMARY

Embodiments of the present disclosure present technological improvements as solutions to one or more of the above-mentioned technical problems recognized by the inventors in conventional systems.

In an aspect, there is provided a processor implemented method for benchmarking asset performance comprising: extracting, by one or more hardware processors, a first set of features comprising domain independent statistical features, from an obtained raw electrocardiography (ECG) time series, wherein the first set of features include (i) self-similarity of the raw ECG time series indicative of a rate of decrease in autocorrelation with an increase in lag between a pair of observations, wherein the self-similarity is measured based on Hurst parameter (H) which is computed by fitting the raw ECG time series into a Fractional Autoregressive Integrated Moving Average (FARIMA(0,d,0)) model by an approximation of the maximum likelihood method and the Hurst parameter is estimated using the relation $H=d+0.5$, wherein d is a degree of differentiating indicative of the number of times the raw ECG time series has a past value subtracted from a current value and (ii) average Maharaj's distance indicative of a moving average factor along with the number of changes in direction of the raw ECG time series, wherein the average Maharaj's distance is based on the Maharaj's distance of the raw ECG time series of an $i^{th}$ subject from a $j^{th}$ coronary heart disease (CHD) subject in a training dataset and nu being the total number of CHD subjects in the training dataset and measures the average dissimilarity of an ECG time series from the CHD population in the training dataset; extracting, by the one or more hardware processors, a second set of features comprising domain specific statistical features pertaining to Heart Rate Variability (HRV), from RR interval time series ($RR_t$) obtained from the raw ECG time series, wherein the second set of features comprise one or more of range, standard deviation, kurtosis, skewness, ratio of spectral power content of the $RR_t$ between an empirically determined range of frequencies, Shannon entropy of the $RR_t$, pNNT indicative of a time domain measure of HRV based on the number of successive RR intervals (m) exceeding time T in an ECG recording of a fixed duration, wherein time T is measured in ms and $\delta RR_t$ time series is indicative of successive RR intervals ($RR_i$-$RR_{i-1}$), Normalized Root Mean Square of Successive Differences (nRMSSD), features from Lorenz plot of the $\delta RR_t$ time series including AnisotropyEvidence and PACEvidence, and features from recurrence plots of the $RR_t$ including recurrence rate (REC), determinism (DET) and mean diagonal line length ($L_{mean}$); and classifying, by the one or more hardware processors, the raw ECG time series into a CHD or a non-CHD candidate based on a complete feature set comprising the first set of features and the second set of features.

In another aspect, there is provided a system comprising: one or more data storage devices operatively coupled to the one or more processors and configured to store instructions configured for execution by the one or more processors to: extract a first set of features comprising domain independent statistical features, from an obtained raw electrocardiography (ECG) time series, wherein the first set of features include (i) self-similarity of the raw ECG time series indicative of a rate of decrease in autocorrelation with an increase in lag between a pair of observations, wherein the self-similarity is measured based on Hurst parameter (H) which is computed by fitting the raw ECG time series into a Fractional Autoregressive Integrated Moving Average (FARIMA(0,d,0)) model by an approximation of the maximum likelihood method and the Hurst parameter is estimated using the relation $H=d+0.5$., wherein d is a degree of differentiating indicative of the number of times the raw ECG time series has a past value subtracted from a current value and (ii) average Maharaj's distance indicative of a moving average factor along with the number of changes in direction of the raw ECG time series, wherein the average Maharaj's distance is based on the Maharaj's distance of the raw ECG time series of an $i^{th}$ subject from a $j^{th}$ coronary heart disease (CHD) subject in a training dataset and nu being the total number of CHD subjects in the training dataset and measures the average dissimilarity of an ECG time series from the CHD population in the training dataset; extract a second set of features comprising domain specific statistical features pertaining to Heart Rate Variability (HRV), from RR interval time series ($RR_t$) obtained from the raw ECG time series, wherein the second set of features comprise one or more of range, standard deviation, kurtosis, skewness, ratio of spectral power content of the $RR_t$ between an empirically determined range of frequencies, Shannon entropy of the $RR_t$, pNNT indicative of a time domain measure of HRV based on the number of successive RR intervals (m) exceeding time T in an ECG recording of a fixed duration, wherein time T is measured in ms and $\delta RR_t$ time series is indicative of successive RR intervals ($RR_i$-$RR_{i-1}$), Normalized Root Mean Square of Successive Differences (nRMSSD), features from Lorenz plot of the $\delta RR_t$ time series including AnisotropyEvidence and PACEvidence, and features from recurrence plots of the $RR_t$ including recurrence rate (REC), determinism (DET) and mean diagonal line length ($L_{mean}$); and classify the raw ECG time series into a coronary heart disease (CHD) or a non-coronary heart disease (non-CHD) candidate based on a complete feature set comprising the first set of features and the second set of features.

In yet another aspect, there is provided a computer program product comprising a non-transitory computer readable medium having a computer readable program embodied therein, wherein the computer readable program, when executed on a computing device, causes the computing device to: extract a first set of features comprising domain independent statistical features, from an obtained raw electrocardiography (ECG) time series, wherein the first set of features include (i) self-similarity of the raw ECG time series indicative of a rate of decrease in autocorrelation with an increase in lag between a pair of observations, wherein the self-similarity is measured based on Hurst parameter (H) which is computed by fitting the raw ECG time series into a Fractional Autoregressive Integrated Moving Average (FARIMA(0,d,0)) model by an approximation of the maximum likelihood method and the Hurst parameter is estimated using the relation H=d+0.5, wherein d is a degree of differentiating indicative of the number of times the raw ECG time series has a past value subtracted from a current value and (ii) average Maharaj's distance indicative of a moving average factor along with the number of changes in direction of the raw ECG time series, wherein the average Maharaj's distance is based on the Maharaj's distance of the raw ECG time series of an $i^{th}$ subject from a $j^{th}$ coronary heart disease (CHD) subject in a training dataset and nu being the total number of CHD subjects in the training dataset and measures the average dissimilarity of an ECG time series from the CHD population in the training dataset; extract a second set of features comprising domain specific statistical features pertaining to Heart Rate Variability (HRV), from RR interval time series ($RR_t$) obtained from the raw ECG time series, wherein the second set of features comprise one or more of range, standard deviation, kurtosis, skewness, ratio of spectral power content of the $RR_t$ between an empirically determined range of frequencies, Shannon entropy of the $RR_t$, pNNT indicative of a time domain measure of HRV based on the number of successive RR intervals (m) exceeding time T in an ECG recording of a fixed duration, wherein time T is measured in ms and $\delta RR_t$ time series is indicative of successive RR intervals ($RR_i$-$RR_{i-1}$), Normalized Root Mean Square of Successive Differences (nRMSSD), features from Lorenz plot of the $\delta RR_t$ time series including AnisotropyEvidence and PACEvidence, and features from recurrence plots of the $RR_t$ including recurrence rate (REC), determinism (DET) and mean diagonal line length ($L_{mean}$); and classify the raw ECG time series into a coronary heart disease (CHD) or a non-coronary heart disease (non-CHD) candidate based on a complete feature set comprising the first set of features and the second set of features.

In an embodiment of the present disclosure, the one or more processors are further configured to extract the second set of features by removal of low frequency baseline drift due to respiration and high frequency noise components before extracting R peaks for obtaining the RR intervals.

In an embodiment of the present disclosure, the one or more processors are further configured to obtain the raw ECG time series by: performing a histogram analyses of an ECG image converted to gray scale, wherein the histogram analyses comprises selective quantization to identify pixels corresponding to an associated ECG signal, lines corresponding to associated vertical and horizontal grid lines and an associated reference pulse and generate a quantized image from the ECG image; performing morphological thinning of the quantized image repeatedly with a predefined kernel size till there is no update in successive thinning operations; detecting and eliminating the vertical and horizontal grid lines, wherein the detecting is based on Hough transform; extracting the reference pulse by matching the quantized image subjected to morphological thinning and eliminating of the grid lines with a template of the reference pulse to identify a zero reference line for the ECG signal, wherein the matching with the template is performed at pixel level using two-dimensional autocorrelation analysis; and performing a pixel value quantization to obtain the raw ECG time series having a time scale and amplitude in voltage derived from the reference pulse.

In an embodiment of the present disclosure, the one or more processors are further configured to perform cubic-spline filtering, on the obtained raw ECG time series, locally at regions needing interpolation due to missing data occurring post image processing operations including the morphological thinning and elimination of the grid lines.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

FIG. 2A and FIG. 2B illustrate an exemplary flow diagram for a computer implemented method for non-invasive detection of coronary heart disease from short single-lead ECG, in accordance with an embodiment of the present disclosure.

DETAILED DESCRIPTION

Figure 1:
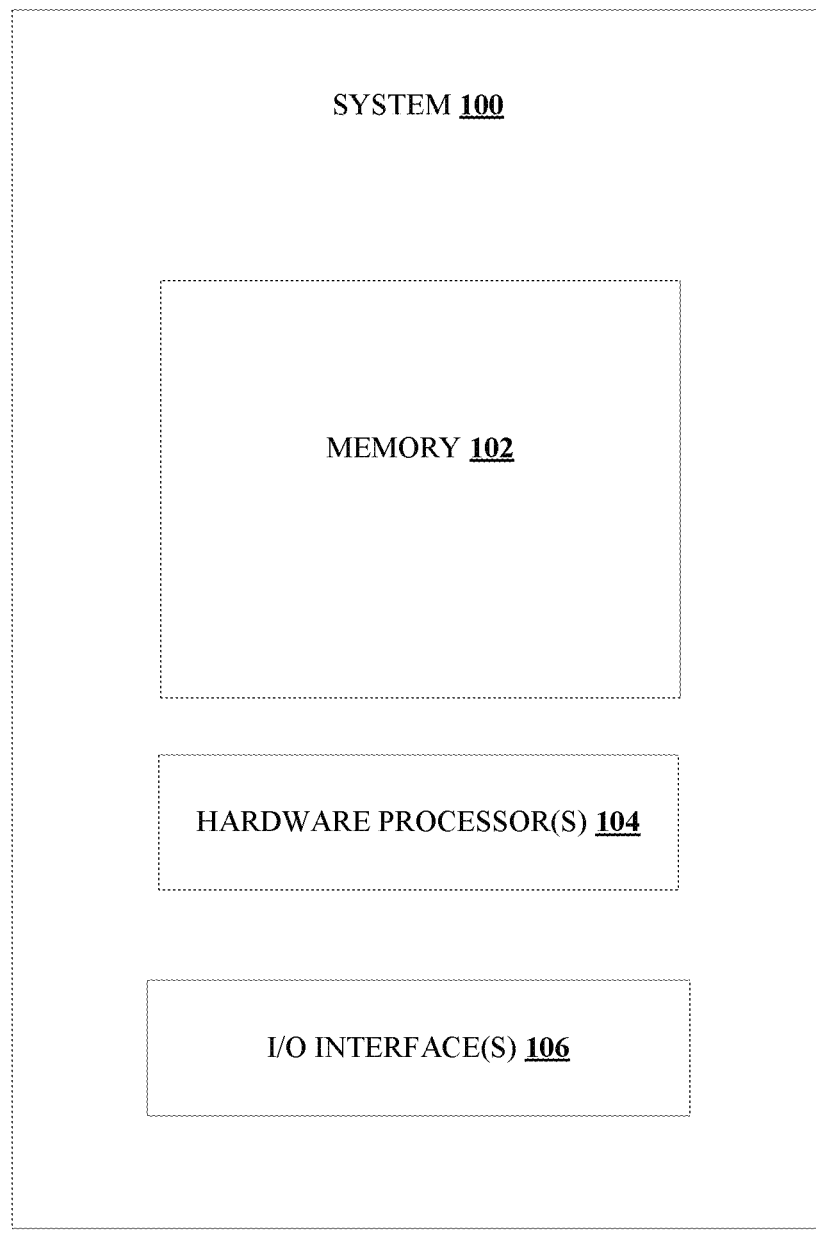
FIG. 1 illustrates an exemplary block diagram of a system for non-invasive detection of coronary heart disease from short single-lead electrocardiography (ECG), in accordance with an embodiment of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Coronary Heart Disease (CHD) is a major cause of death today and accordingly, automatic non-invasive detection of CHD is of immense importance. In accordance with the present disclosure, systems and methods described hereinafter extract electrocardiography (ECG) time series from ECG images corresponding to short duration ECG obtained from commercially available low-cost single lead ECG devices. Further, in accordance with the present disclosure, domain independent statistical features along with domain specific features are used for classifying CHD. In the context of the present disclosure, the expressions Coronary Heart Disease (CHD) and Coronary Artery Disease (CAD) may be used interchangeably.

Referring now to the drawings, and more particularly to FIG. 1 through FIG. 6 where similar reference characters denote corresponding features consistently throughout the figures, there are shown preferred embodiments and these embodiments are described in the context of the following exemplary system and/or method.

FIG. 1 illustrates an exemplary block diagram of a system 100 for non-invasive detection of coronary heart disease from short single-lead electrocardiography (ECG) in accordance with an embodiment of the present disclosure. In an embodiment, the system 100 includes one or more processors 104, communication interface device(s) or input/output (I/O) interface(s) 106, and one or more data storage devices or memory 102 operatively coupled to the one or more processors 104. The one or more processors 104 that are hardware processors can be implemented as one or more microprocessors, microcomputers, microcontrollers, digital signal processors, central processing units, state machines, graphics controllers, logic circuitries, and/or any devices that manipulate signals based on operational instructions. Among other capabilities, the processor(s) are configured to fetch and execute computer-readable instructions stored in the memory. In the context of the present disclosure, the expressions 'processors' and 'hardware processors' may be used interchangeably. In an embodiment, the system 100 can be implemented in a variety of computing systems, such as laptop computers, notebooks, hand-held devices, workstations, mainframe computers, servers, a network cloud and the like.

The I/O interface(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface(s) can include one or more ports for connecting a number of devices to one another or to another server.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, one or more modules (not shown) of the system 100 can be stored in the memory 102.

Figure 2B:
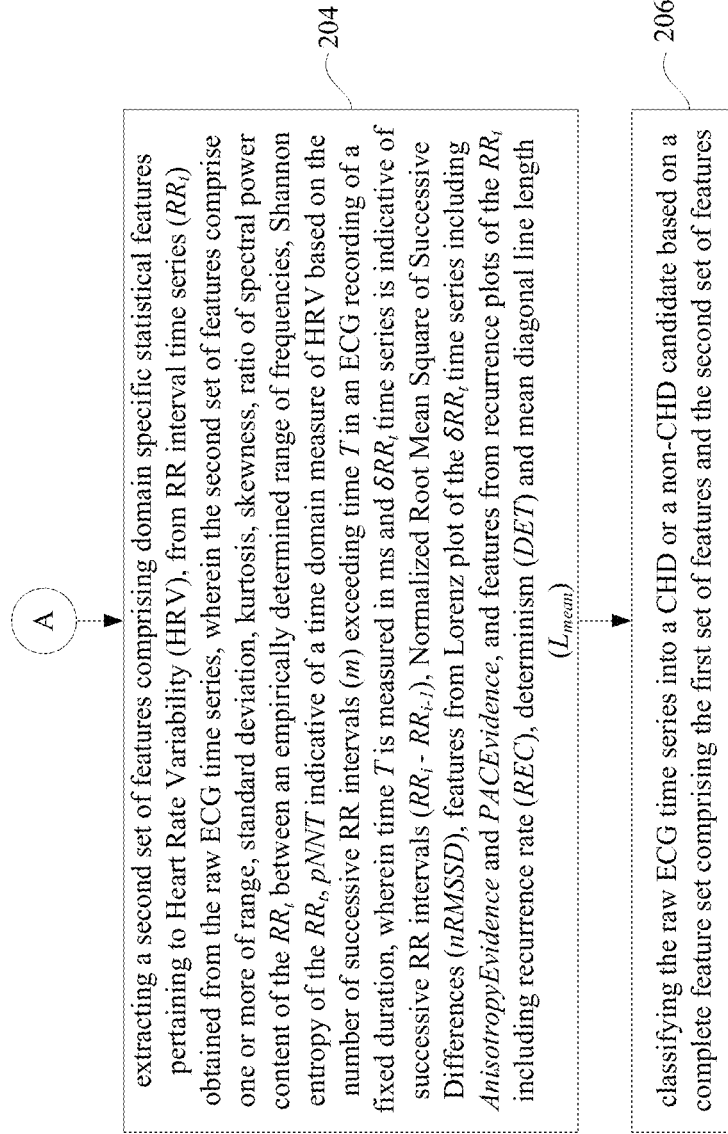

FIG. 2A and FIG. 2B illustrate an exemplary flow diagram for a computer implemented method 200 for non-invasive detection of coronary heart disease from short single-lead ECG, in accordance with an embodiment of the present disclosure. In an embodiment, the system 100 includes one or more data storage devices or memory 102 operatively coupled to the one or more processors 104 and is configured to store instructions configured for execution of steps of the method 200 by the one or more processors 104. The steps of the method 200 will now be explained in detail with reference to the components of the system 100 of FIG. 1. Although process steps, method steps, techniques or the like may be described in a sequential order, such processes, methods and techniques may be configured to work in alternate orders. In other words, any sequence or order of steps that may be described does not necessarily indicate a requirement that the steps be performed in that order. The steps of processes described herein may be performed in any order practical. Further, some steps may be performed simultaneously.

Raw ECG signal, obtained from an individual is represented as a time series of n real valued variables $ecg_r=\{ecg_1, ecg_2, \ldots ecg_n\}$. In accordance with an embodiment of the present disclosure, the one or more processors 104 are configured to extract, at step 202, a first set of features comprising domain independent statistical features, from an obtained raw ECG time series $ecg_r$. In accordance with an embodiment of the present disclosure, the one or more processors 104 are configured to extract, at step 204, a second set of features comprising domain specific statistical features pertaining to Heart Rate Variability (HRV), from RR (peak to peak) interval time series $RR_t=\{RR_1, RR_2, \ldots, RR_m\}$ obtained from the raw ECG time series $ecg_r$, where m denotes the number of RR intervals in an ECG recording. In accordance with an embodiment of the present disclosure, the one or more processors 104 are configured to classify, at step 206, the raw ECG time series into a CHD or a non-CHD candidate based on a complete feature set comprising the first set of features and the second set of features.

Initially, all features are ranked according to their significance with respect to ground truth labels (CHD and non-CHD) based on Maximal Information Coefficient (MIC). MIC is a statistical tool, used for measuring the strength of association between two variables based on mutual information over binning of the data. A higher value of MIC indicates a stronger relationship. Top 20 features from the ranked list are empirically found to produce optimum classification performance. The selected features can be broadly classified into two categories as features derived from the RR interval time series and features derived from the raw ECG time series. Furthermore, features derived from Lorenz Plot and features derived from recurrence plots are also features categorized under features derived from the RR interval time series.

Inherent properties of an ECG waveform often contain discriminating information regarding disease classification. These are often present even in a short recording. In accordance with an embodiment of the present disclosure, the first set of features from the raw ECG time series include self-similarity of the raw ECG time series and average Maharaj's distance. The self-similarity is indicative of a rate of decrease in autocorrelation with an increase in lag between a pair of observations. In accordance with an embodiment of the present disclosure, the self-similarity may be measured based on Hurst parameter (H) which is computed by fitting the raw ECG time series into a Fractional Autoregressive Integrated Moving Average (FARIMA (0,d,0)) model by an approximation of the maximum likelihood method and the Hurst parameter is estimated using the relation H=d+0.5, wherein d is a degree of differentiating indicative of the number of times the raw ECG time series has a past value subtracted from a current value. Conventionally, d is computed using a periodograms that requires computing power spectral density of the ECG signal. In accordance with the present disclosure, the raw ECG time series is employed without computing the periodograms. The average Maharaj's distance is indicative of a moving average factor along with the number of changes in direction of the raw ECG time series. In statistical data analysis, Maharaj's distance captures a desired similarity metric across spatial entities. An autoregressive-moving-average (ARMA) time series $Y_t$ with autoregression parameter p and moving average parameter r may be defined as:

$$Y_t = \lambda + \sum_{i=1}^{p} \psi_i Y_{t-i} + \sum_{i=1}^{r} \theta_i \epsilon_{t-i} + \epsilon_t \quad (1)$$

wherein $\lambda$ is a constant, $\epsilon_t$ is white noise, $\psi_i$ represents the autoregression parameters and $\theta_i$ represents the moving average parameter. For ARMA processes, discrepancy measurement based on hypotheses testing may be used to determine whether two time series $X_t$ and $Y_t$ have significantly different generating processes. The output metric of this process is called the Maharaj's distance and is used in the present disclosure to find whether the time series are similar to each other. A p-value is computed which lies between 0 and 1. A p-value close to 1 indicates the two time series are similar, and a value close to 0 indicates they are different.

In accordance with an embodiment of the present disclosure, the average Maharaj's distance is based on the Maharaj's distance $MD_{ij}$ of the raw ECG time series of an $i^{th}$ subject from a $j^{th}$ CHD subject in a training dataset and nu being the total number of CHD subjects in the training dataset and measures the average dissimilarity of an ECG time series from the CHD population in the training dataset. Accordingly, average Maharaj's distance (AMD) for the raw ECG time signal of the $i^{th}$ subject (both training and test dataset), is measured as $$AMD_i = \sum_{j \neq i}^{nu} MD_{ij} / (nu - 1) \quad (2)$$

In accordance with an embodiment of the present disclosure, other features that may be comprised in the first set of features include one or more of kurtosis, skewness, Shannon's entropy and Tsallis entropy. Tsallis entropy may be calculated as:

$$S_q(x) = \frac{k}{q-1}\left(1 - \sum_{c=1}^{M} prob_c\right) \quad (3)$$

wherein $prob_c$ measures the probability of each of M bins of a normalized histogram of $ecg_t$. k(Boltzmann's constant)=1 and q(entropic-index)=2 are predefined parameters.

In accordance with the present disclosure, features pertaining to HRV are extracted from the RR interval time series at step 204 as the second set of features. In an embodiment, the second set of features may comprise one or more of range, standard deviation, kurtosis, skewness, ratio of spectral power content of the $RR_t$ between an empirically determined range of frequencies, Shannon entropy of the $RR_t$, pNNT indicative of a time domain measure of HRV based on the number of successive RR intervals (m) exceeding time T in an ECG recording of a fixed duration, wherein time T is measured in ms and $\delta RR_t$ time series is indicative of successive RR intervals ($RR_i$-$RR_{i-1}$), Normalized Root Mean Square of Successive Differences (nRMSSD), features from Lorenz plot of the $\delta RR_t$ time series including AnisotropyEvidence and PACEvidence, and features from recurrence plots of the $RR_t$ including recurrence rate (REC), determinism (DET) and mean diagonal line length ($L_{mean}$).

Shannon entropy of $RR_t$ is a discriminative marker and may be represented as:

$$E_{sh} = -\sum_{b=1}^{N} pr_b \log pr_b \quad (4)$$

Initially a normalized histogram of N bins is created from $RR_t$. Empirical probability of $b^{th}$ bin of the histogram is denoted by $pr_b$. Here $b \in 1 \ldots N$ and $\Sigma_{b=1}^{N} pr_b$. The value of $E_{sh}$ becomes higher due to irregularities in HRV.

The parameters pNNT calculated for measuring the irregularities in $RR_t$ may be pNN20, pNN50 and pNN75. In general, pNNT is measured using the following set of equations:

$$\left[\delta_i = \begin{cases} 1, & if \ |RR_{i+1} - RR_i| > T \\ 0, & otherwise \end{cases}\right. \quad (5)$$

$$pNNT = \frac{\sum_i \delta_i}{m} \quad (6)$$

pNN20 and pNN50 are known in the art. However, pNN75 (successive RR interval difference exceeds 75 ms) as provided in the present disclosure is identified as a critical marker for classifying CHD.

In accordance with an embodiment of the present disclosure, Normalized Root Mean Square of Successive Differences (nRMSSD) derived from $RR_t$ may also be comprised in the second set of features, wherein nRMSSD is represented as:

$$nRMSSD = \frac{\sqrt{\frac{1}{m-1}\sum_{i=1}^{m-1} RR_{i+1} - RR_i^2}}{\overline{HR}} \quad (7)$$

wherein $\overline{HR}$ measures the average heart rate in an ECG recording.

$\delta RR_t = \{\delta RR_1, \delta RR_2, \ldots\}$ is a real valued time series wherein $\delta RR_i = RR_i - RR_{i-1}$. Lorenz plot of $\delta RR_t$ is a scatter plot of $\delta RR_{i-1}$ versus $\delta RR_i$ for finding the uncorrelated nature of RR intervals. In accordance with the present disclosure, AnisotropyEvidence and PACEvidence may comprise the second set of features.

Figure 3:
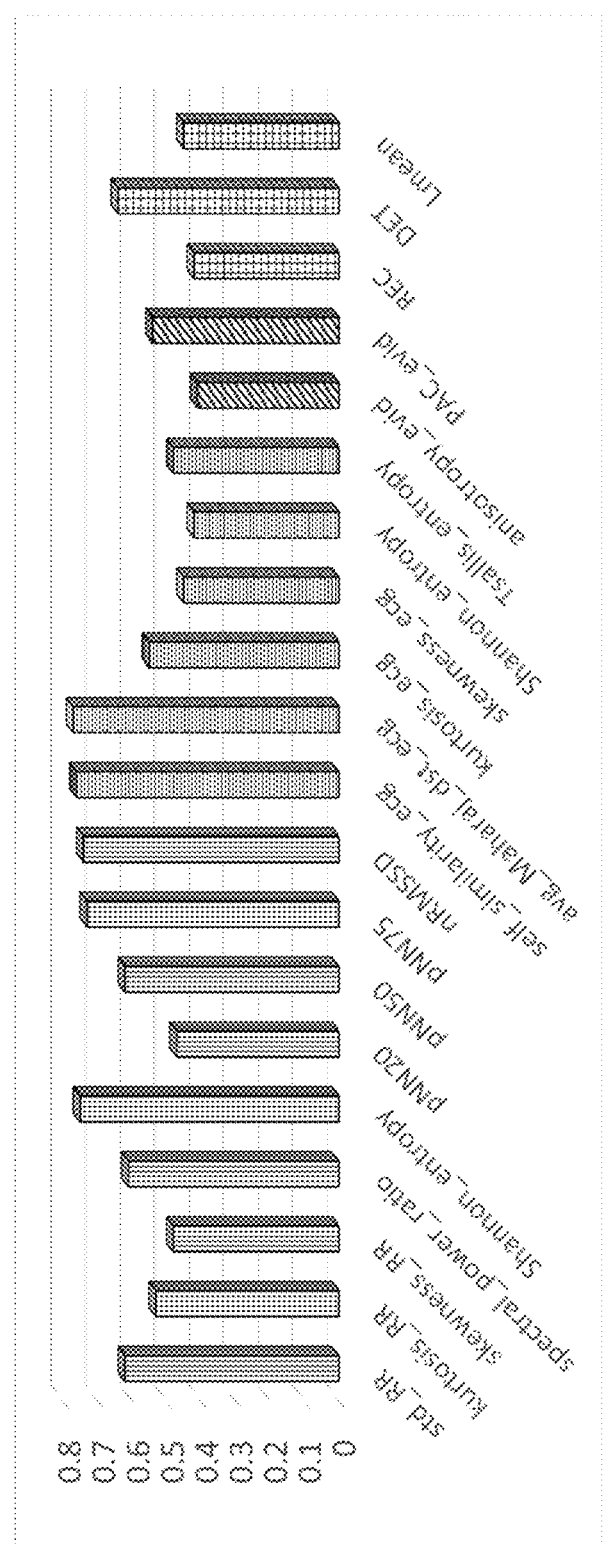
FIG. 3 illustrates Maximal Information Coefficient (MIC) values of ECG features with respect to ground truth labels, in accordance with an embodiment of the present disclosure.

Recurrence plot is used for non-linear data analysis. In accordance with the present disclosure, the three parameters that may comprise the second set of features include the recurrence rate (REC), the determinism (DET) and the mean diagonal line length ($L_{mean}$) extracted from the recurrence plot of $RR_i$. FIG. 3 illustrates Maximal Information Coefficient (MIC) values of ECG features with respect to ground truth labels, in accordance with an embodiment of the present disclosure. Some of the illustrated features may be used for classifying the raw ECG time series. It may be observed that along with HRV features many of the time series features are strongly related with the ground truth. The features of the present disclosure viz., self-similarity and average Maharaj's distance are found to be among the top ranked features with MIC values above 0.7.

In an embodiment of the present disclosure, the step 204 of obtaining a second set of features comprises removal of low frequency baseline drift due to respiration and high frequency noise components before extracting R peaks for obtaining the RR intervals.

Experimental Dataset

The CHD population of the experimental dataset contains angiography-proven CHD patients of varying heart blockages. On the other hand, the non-CHD population contains both healthy subjects with no self and family cardiac history as well as patients having non-cardiac diseases. The entire dataset is collected using AliveCor Kardia device from Fortis hospital, Kolkata, India under the supervision of practicing clinicians and approved by the hospital ethics committee. The dataset contains ECG from 130 consenting unique subjects, including 77 CHD and 53 non-CHD subjects. Wide variation in patient demography (age, BMI) is ensured in both the classes. The duration of recording, collected from every subject is fixed for 30 seconds. All subjects are ensured to be in complete rest position during data collection. AliveCor Kardia is a low-cost portable device that records single-lead ECG of clinical quality. The device communicates to AliveCor proprietary software, installed on a smart phone for instant display and stores the recorded ECG in a remote server as a PDF image.

Figure 5A:
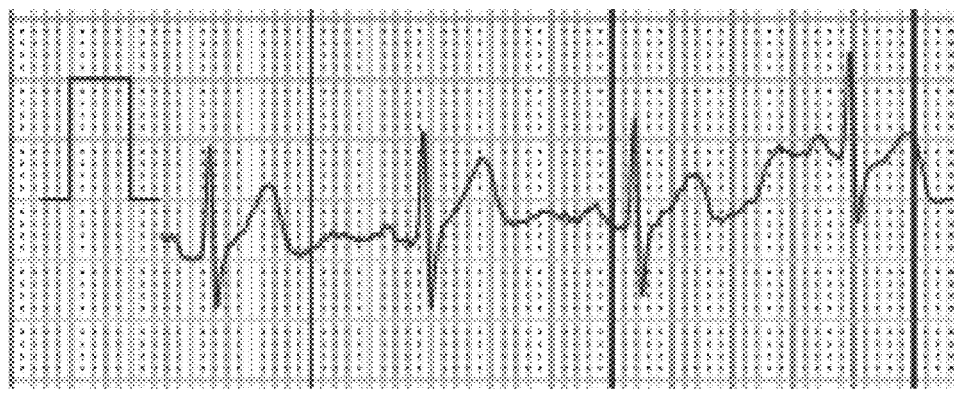
FIG. 5A illustrates a sample ECG image as known in the art.

In an embodiment of the present disclosure, the step 202 of extracting the first set of features is preceded by obtaining the raw ECG time series. Extraction of raw time series from the PDF image is a next step for subsequent feature extraction and classification. Initially, the recorded PDF is converted to a PNG image for analysis. The ECG is stored as a series of images put on top of a grid based layout (as shown in FIG. 5A). The layout is partitioned into large grids of 5 mm×5 mm boxes representing 200 ms in horizontal axis (time axis) and 0.5 mV in vertical axis. Each large grid is further divided into smaller grids of 1 mm×1 mm, representing 40 ms in time and 0.1 mV in amplitude. There exists a reference pulse of 1 mV in amplitude providing the reference for zero voltage. The ECG printable images are analyzed with respect to this reference. The ECG is extracted from the images through a combination of certain image and signal processing steps as described hereinafter.

Figure 4:
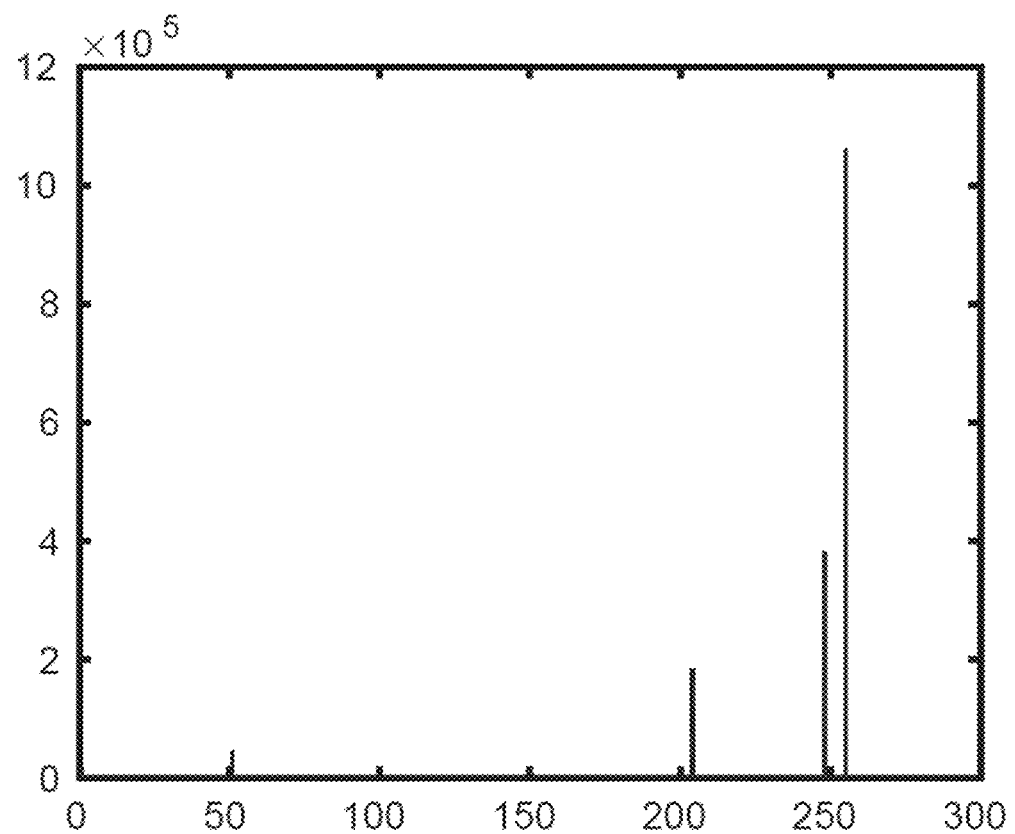
FIG. 4 illustrates a histogram of gray scale pixel values in an ECG image, in accordance with an embodiment of the present disclosure.
Figure 5B:
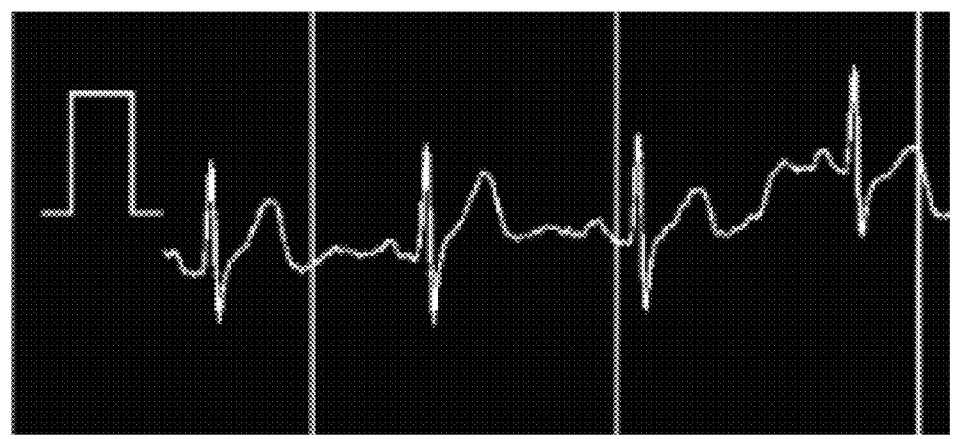
FIG. 5B illustrates an output of selective quantization based on histogram analyses, in accordance with an embodiment of the present disclosure.

The colored ECG images are converted to gray scale. A histogram analysis is then performed on the image. FIG. 4 illustrates a histogram of gray scale pixel values in an ECG image, in accordance with an embodiment of the present disclosure. In accordance with an embodiment of the present disclosure, the histogram analyses comprises selective quantization to identify pixels corresponding to an associated ECG signal, lines corresponding to associated vertical and horizontal grid lines and an associated reference pulse and generate a quantized image from the ECG image. It is found empirically that the pixels ranging between 40 and 180 constitute the ECG signal, lines corresponding to the large grid lines (both horizontal and vertical) and the reference pulse. Any pixel outside that range is quantized to zero. FIG. 5A illustrates a sample ECG image as known in the art and FIG. 5B illustrates an output of selective quantization based on the histogram analyses, in accordance with an embodiment of the present disclosure.

In accordance with an embodiment of the present disclosure, morphological thinning is performed on the quantized image repeatedly with a pre-defined kernel size till there is no update in successive thinning operations. In an embodiment, the quantized image has a kernel size 5×5. Thinning of an image A by a structuring element (kernel) $\{B\}=\{B^1, B^2, \ldots B^n\}$ is defined in terms of morphological hit-or-miss transform $A \circledast B$. The thinning operation maybe represented as:

$$A \otimes \{B\} = ((((A \otimes B^1) \otimes B^2) \ldots ) \otimes B^n) \quad (8)$$

A is thinned by one pass with $B^1$, followed by one pass with $B^2$, and so on until $B^n$. The entire process is repeated until no further changes occur in A. Each pass is performed using $$A \otimes B^i = A - (A \circledast B^i) = A \cap (A \circledast B^i)^c \quad (9)$$

Figure 5C:
FIG. 5C illustrates an output of morphological thinning and removal of large grid lines in accordance with an embodiment of the present disclosure.

In accordance with an embodiment of the present disclosure, the horizontal and vertical lines for the large grids are detected using Hough transform and then removed. FIG. 5C illustrates an output of morphological thinning and removal of large grid lines in accordance with an embodiment of the present disclosure.

In accordance with an embodiment of the present disclosure, the reference pulse is extracted by matching the quantized image subjected to morphological thinning and eliminating of the grid lines with a template of the reference pulse and then the zero reference line is identified for the ECG signal. Template matching is done in pixel level using two-dimensional autocorrelation analysis. FIG. 5C illustrates the cleaned image corresponding to the ECG signal. A pixel value quantization of the output of morphological operation gives raw ECG time series having a time scale and amplitude in voltage derived from the reference pulse.

Figure 6:
FIG. 6 illustrates missing data needing interpolation in a sample of the obtained raw ECG time series, in accordance with an embodiment of the present disclosure.

After the extraction of the ECG signal, there may be some missing points due to the image processing operations which include thinning, removal of grid lines which need to be corrected. FIG. 6 illustrates missing data needing interpolation in a sample of the obtained raw ECG time series, in accordance with an embodiment of the present disclosure. In an embodiment, a cubic-spline filtering is performed locally in the region of missing data to generate the interpolated ECG signal.

Classification and Experimental Results

Sensitivity (Se) and specificity (Sp) of classifying CHD patients are calculated and the final performance metric is reported by assigning equal weight to both the parameters, as shown below.

$$MAcc = \frac{Se + Sp}{2} \quad (10)$$

wherein Se=TP/(TP+FN) and Sp=TN/(TN+FP), TP being the True Positives, FN being the False Negatives, TN being the True Negatives and FP being the False Positives. The metric MAcc is a better performance estimator than classification accuracy Acc=(TP+TN)/(TP+TN+FP+FN) on skewed datasets.

Several supervised classifiers were explored in this study. The boosting algorithm RUSBoost, based on decision tree is found to produce optimum performance. Boosting is a powerful supervised learning technique that often improves the classification accuracy by iteratively creating an ensemble of weak learners from the training dataset, combined together to form the final learning model. Random Undersampling Boost (RUSBoost) is designed to work on unbalanced datasets. Training examples are randomly removed from the majority class until a desired class distribution is achieved.

Table I shows a performance comparison of different classifiers, Support Vector Machine (SVM) with Radial Basis Function (RBF) kernel, Random Forest (RF), AdaBoost and RUSBoost, all created based on the complete feature set of the present disclosure.

TABLE I

Performance of different supervised classifiers in mean ± std, using 5-fold Cross Validation, based on the complete feature set of the present disclosure.

| Classifier | Se | Sp | MAcc |
|---|---|---|---|
| SVM, RBF | 0.72 ± 0.23 | 0.31 ± 0.17 | 0.51 ± 0.19 |
| SVM, RBF with SMOTE | 0.66 ± 0.18 | 0.58 ± 0.11 | 0.63 ± 0.13 |
| Random Forest (RF) | 0.80 ± 0.16 | 0.48 ± 0.21 | 0.65 ± 0.18 |
| RF with SMOTE | 0.75 ± 0.11 | 0.68 ± 0.13 | 0.73 ± 0.11 |
| AdaBoost | 0.87 ± 0.06 | 0.70 ± 0.10 | 0.78 ± 0.08 |
| AdaBoost with SMOTE | 0.82 ± 0.06 | 0.76 ± 0.05 | 0.80 ± 0.05 |
| RUSBoost | 0.85 ± 0.07 | 0.82 ± 0.06 | 0.84 ± 0.07 |

Hyperparameters for different classifiers are tuned empirically. A total of 50 tress are used in the RF classifier. 60 ensemble learning cycles are used in both AdaBoost and RUSBoost classifiers. Sensitivity, specificity and MAcc in detecting CHD are reported in mean±std format by applying 5-fold cross validation on the dataset. Synthetic Minority Oversampling Technique (SMOTE) is an algorithm for handling skewed dataset based on creating new minority class examples extrapolating between existing examples. Table I shows that the detection accuracy of minority class (non-CHD class) significantly improves by applying SMOTE before SVM, RF and AdaBoost. Thus overall specificity enhances without affecting sensitivity much, resulting in an improved MAcc. However, these three classifiers are outperformed by RUSBoost even after applying SMOTE. A possible reason is, oversampling via duplicating or synthetically generating minority training class may lead to an overfit. Whereas RUSBoost randomly removes samples from the majority class in every iteration before creating the ensemble model. This enhances both sensitivity and specificity, resulting in the maximum value of MAcc.

Table II shows that the method of the present disclosure outperforms Dua et al. "Novel classification of coronary artery disease using heart rate variability analysis," *Journal of Mechanics in Medicine and Biology*, vol. 12, no. 4 (2012), designed based on HRV related features. Since the method in Dua et al. is reported to outperform other available methodologies, these are not considered for performance comparison.

TABLE II

Comparison with other methodologies in mean ± std using 5-fold Cross Validation

| Method | Se | Sp | MAcc |
|---|---|---|---|
| Dua et al. | 0.80 ± 0.10 | 0.65 ± 0.14 | 0.75 ± 0.12 |
| Method of the present disclosure without the first set of features + RUSBoost | 0.75 ± 0.12 | 0.72 ± 0.16 | 0.73 ± 0.14 |
| Method of the present disclosure with complete feature set + RUSBoost | 0.85 ± 0.07 | 0.82 ± 0.06 | 0.84 ± 0.07 |

Table II also shows that performance of the method of the present disclosure significantly drops if only HRV related features are selected without considering raw ECG time series features. The complete feature set not only yields the highest MAcc, but also lesser standard deviation across the folds of cross validation for all the three metrics thereby justifying the need for combing the first feature set and the second feature set of the present disclosure.

The present disclosure thus enables classifying CHD subjects from short single-lead ECG, recorded using commercially available low cost portable device. Particularly, two statistical features derived from the ECG time series are disclosed which when combined with the other features enhance accuracy of classification as shown above.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A processor implemented method for non-invasive detection of coronary heart disease (200), the method comprising the steps of:
   extracting, by one or more hardware processors, a first set of features comprising domain independent statistical features, from an obtained raw electrocardiography (ECG) time series (202), wherein the first set of features include (i) self-similarity of the raw ECG time series indicative of a rate of decrease in autocorrelation with an increase in lag between a pair of observations, wherein the self-similarity is measured based on Hurst parameter (H) which is computed by fitting the raw ECG time series into a Fractional Autoregressive Integrated Moving Average (FARIMA(0,d,0)) model by an approximation of a maximum likelihood method and the Hurst parameter is estimated using the relation H=d+0.5, wherein d is a degree of differentiating indicative of the number of times the raw ECG time series has a past value subtracted from a current value and (ii) average Maharaj's distance indicative of a moving average factor along with a number of changes in direction of the raw ECG time series, wherein the average Maharaj's distance is based on the average Maharaj's distance of the raw ECG time series of an $i^{th}$ subject from a $j^{th}$ coronary heart disease (CHD) subject in a training dataset and nu being the total number of CHD subjects in the training dataset and measures an average dissimilarity of an ECG time series from the CHD population in the training dataset;
   extracting, by the one or more hardware processors, a second set of features comprising domain specific statistical features pertaining to Heart Rate Variability (HRV), from RR interval time series ($RR_t$) obtained from the raw ECG time series (204), wherein the second set of features comprise one or more of range, standard deviation, kurtosis, skewness, ratio of spectral power content of the $RR_t$ between an empirically determined range of frequencies, Shannon entropy of the $RR_t$, pNNT indicative of a time domain measure of HRV based on a number of successive RR intervals (m) exceeding time T in an ECG recording of a fixed duration, wherein time T is measured in ms and $\delta RR_t$ time series is indicative of successive RR intervals ($RR_i RR_{i-1}$), Normalized Root Mean Square of Successive Differences ($_nRMSSD$), features from Lorenz plot of the $\delta RR_t$ time series including AnisotropyEvidence and PACEvidence, and features from recurrence plots of the $RR_t$ including recurrence rate (REC), determinism (DET) and mean diagonal line length ($L_{mean}$), wherein the step of extracting the second set of features comprises removal of low frequency baseline drift due to respiration and high frequency noise components before extracting R peaks for obtaining the RR intervals; and
   classifying, by the one or more hardware processors, the raw ECG time series into a CHD or a non-CHD candidate based on a complete feature set comprising the first set of features and the second set of features (206).

2. The processor implemented method of claim 1, wherein the step of extracting the first set of features is preceded by obtaining the raw ECG time series by:
   performing a histogram analyses of an ECG image converted to gray scale, wherein the histogram analyses comprises selective quantization to identify pixels corresponding to an associated ECG signal, lines corresponding to associated vertical and horizontal grid lines and an associated reference pulse and generate a quantized image from the ECG image;
   performing morphological thinning of the quantized image repeatedly with a pre-defined kernel size till there is no update in successive thinning operations;
   detecting and eliminating the vertical and horizontal grid lines, wherein the detecting is based on Hough transform;
   extracting the reference pulse by matching the quantized image subjected to morphological thinning and eliminating of the vertical and horizontal grid lines with a template of the reference pulse to identify a zero reference line for the ECG signal, wherein the matching with the template is performed at pixel level using two-dimensional autocorrelation analysis; and performing a pixel value quantization to obtain the raw ECG time series having a time scale and amplitude in voltage derived from the reference pulse.

3. The processor implemented method of claim 2 further comprising performing cubic-spline filtering, on the obtained raw ECG time series, locally at regions needing interpolation due to missing data occurring post image processing operations including the morphological thinning and elimination of the vertical and horizontal grid lines.

4. A system comprising:
one or more data storage devices operatively coupled to one or more hardware processors and configured to store instructions configured for execution by the one or more hardware processors to:
extract a first set of features comprising domain independent statistical features, from an obtained raw electrocardiography (ECG) time series, wherein the first set of features include (i) self-similarity of the raw ECG time series indicative of a rate of decrease in autocorrelation with an increase in lag between a pair of observations, wherein the self-similarity is measured based on Hurst parameter (H) which is computed by fitting the raw ECG time series into a Fractional Autoregressive Integrated Moving Average (FARIMA(0,d,0)) model by an approximation of a maximum likelihood method and the Hurst parameter is estimated using the relation H=d+0.5, wherein d is a degree of differentiating indicative of the number of times the raw ECG time series has a past value subtracted from a current value and (ii) average Maharaj's distance indicative of a moving average factor along with a number of changes in direction of the raw ECG time series, wherein the average Maharaj's distance is based on the average Maharaj's distance of the raw ECG time series of an $i^{th}$ subject from a $j^{th}$ coronary heart disease (CHD) subject in a training dataset and nu being the total number of CHD subjects in the training dataset and measures an average dissimilarity of an ECG time series from the CHD population in the training dataset;
extract a second set of features comprising domain specific statistical features pertaining to Heart Rate Variability (HRV), from RR interval time series ($RR_t$) obtained from the raw ECG time series, wherein the second set of features comprise one or more of range, standard deviation, kurtosis, skewness, ratio of spectral power content of the $RR_t$ between an empirically determined range of frequencies, Shannon entropy of the $RR_t$, pNNT indicative of a time domain measure of HRV based on a number of successive RR intervals (m) exceeding time T in an ECG recording of a fixed duration, wherein time T is measured in ms and $\delta RR_t$ time series is indicative of successive RR intervals ($RR_t$-$RR_{i-1}$), Normalized Root Mean Square of Successive Differences ($_nRMSSD$), features from Lorenz plot of the $\delta RR_t$ time series including AnisotropyEvidence and PACEvidence, and features from recurrence plots of the $RR_t$ including recurrence rate (REC), determinism (DET) and mean diagonal line length ($L_{mean}$), wherein the step of extracting the second set of features comprises removal of low frequency baseline drift due to respiration and high frequency noise components before extracting R peaks for obtaining the RR intervals; and classify the raw ECG time series into a coronary heart disease (CHD) or a non-coronary heart disease (non-CHD) candidate based on a complete feature set comprising the first set of features and the second set of features.

5. The system of claim 4, wherein the one or more processors are further configured to obtain the raw ECG time series by:
performing a histogram analyses of an ECG image converted to gray scale, wherein the histogram analyses comprises selective quantization to identify pixels corresponding to an associated ECG signal, lines corresponding to associated vertical and horizontal grid lines and an associated reference pulse and generate a quantized image from the ECG image;
performing morphological thinning of the quantized image repeatedly with a pre-defined kernel size till there is no update in successive thinning operations;
detecting and eliminating the vertical and horizontal grid lines, wherein the detecting is based on Hough transform;
extracting the reference pulse by matching the quantized image subjected to morphological thinning and eliminating of the vertical and horizontal grid lines with a template of the reference pulse to identify a zero reference line for the ECG signal, wherein the matching with the template is performed at pixel level using two-dimensional autocorrelation analysis; and
performing a pixel value quantization to obtain the raw ECG time series having a time scale and amplitude in voltage derived from the reference pulse.

6. The system of claim 5, wherein the one or more processors are further configured to perform cubic-spline filtering, on the obtained raw ECG time series, locally at regions needing interpolation due to missing data occurring post image processing operations including the morphological thinning and elimination of the vertical and horizontal grid lines.

7. A computer program product comprising a non-transitory computer readable medium having a computer readable program embodied therein, wherein the computer readable program, when executed on a computing device, causes the computing device to:
extract a first set of features comprising domain independent statistical features, from an obtained raw electrocardiography (ECG) time series, wherein the first set of features include (i) self-similarity of the raw ECG time series indicative of a rate of decrease in autocorrelation with an increase in lag between a pair of observations, wherein the self-similarity is measured based on Hurst parameter (H) which is computed by fitting the raw ECG time series into a Fractional Autoregressive Integrated Moving Average (FARIMA(0,d,0)) model by an approximation of a maximum likelihood method and the Hurst parameter is estimated using the relation H=d+0.5, wherein d is a degree of differentiating indicative of the number of times the raw ECG time series has a past value subtracted from a current value and (ii) average Maharaj's distance indicative of a moving average factor along with a number of changes in direction of the raw ECG time series, wherein the average Maharaj's distance is based on the average Maharaj's distance of the raw ECG time series of an $i^{th}$ subject from a $j^{th}$ coronary heart disease (CHD) subject in a training dataset and nu being the total number of CHD subjects in the training dataset and measures an average dissimilarity of an ECG time series from the CHD population in the training dataset;

extract a second set of features comprising domain specific statistical features pertaining to Heart Rate Variability (HRV), from RR interval time series ($RR_t$) obtained from the raw ECG time series, wherein the second set of features comprise one or more of range, standard deviation, kurtosis, skewness, ratio of spectral power content of the $RR_t$ between an empirically determined range of frequencies, Shannon entropy of the $RR_t$, pNNT indicative of a time domain measure of HRV based on a number of successive RR intervals (m) exceeding time T in an ECG recording of a fixed duration, wherein time T is measured in ms and $\delta RR_t$ time series is indicative of successive RR intervals ($RR_i - RR_{i-1}$), Normalized Root Mean Square of Successive Differences ($_nRMSSD$), features from Lorenz plot of the $\delta RR_t$ time series including AnisotropyEvidence and PACEvidence, and features from recurrence plots of the $RR_t$ including recurrence rate (REC), determinism (DET) and mean diagonal line length ($L_{mean}$), wherein the step of extracting the second set of features comprises removal of low frequency baseline drift due to respiration and high frequency noise components before extracting R peaks for obtaining the RR intervals; and classify the raw ECG time series into a coronary heart disease (CHD) or a non-coronary heart disease (non-CHD) candidate based on a complete feature set comprising the first set of features and the second set of features.

8. The computer program product of claim 7, wherein the computer readable program further causes the computing device to: perform cubic-spline filtering, on the obtained raw ECG time series, locally at regions needing interpolation due to missing data occurring post image processing operations including the morphological thinning and elimination of the vertical and horizontal grid lines.

* * * * *